United States Patent
Nyabero et al.

(10) Patent No.: US 10,729,341 B1
(45) Date of Patent: Aug. 4, 2020

(54) NEUROSTIMULATION SYSTEM (71) Applicant: NewSpring Technologies, LLC, Scottsdale, AZ (US)

(72) Inventors: Wambui Nyabero, Scottsdale, AZ (US); Lucas Nyabero, Scottsdale, AZ (US)

(*) Notice: Subject to any disclaimer, the term of this patent is extended or adjusted under 35 U.S.C. 154(b) by 1117 days.

(21) Appl. No.: 14/992,000

(22) Filed: Jan. 10, 2016

Related U.S. Application Data (60) Provisional application No. 62/102,071, filed on Jan. 11, 2015.

(51) Int. Cl.
*A61B 5/04* (2006.01)
*A61B 5/05* (2006.01)
*A61B 5/00* (2006.01)

(52) U.S. Cl.
CPC ............ *A61B 5/04001* (2013.01); *A61B 5/05* (2013.01); *A61B 5/4041* (2013.01); *A61B 5/6825* (2013.01); *A61B 5/6828* (2013.01); *A61B 5/6829* (2013.01); *A61B 5/7282* (2013.01)

(58) Field of Classification Search
CPC ..... A61B 5/04001; A61B 5/05; A61B 5/4041; A61B 5/6825; A61B 5/6828; A61B 5/6829; A61B 5/7282
USPC ........................................................ 600/384
See application file for complete search history.

(56) References Cited

U.S. PATENT DOCUMENTS

| | | | | |
|---|---|---|---|---|
| 9,332,918 | B1* | 5/2016 | Buckley | A61B 5/04001 |
| 2005/0131317 | A1* | 6/2005 | Oddsson | A61B 5/6829 600/592 |
| 2011/0301670 | A1* | 12/2011 | Gross | A61N 1/36071 607/62 |
| 2013/0085420 | A1* | 4/2013 | Feinstein | A61N 1/0468 601/5 |
| 2014/0257436 | A1* | 9/2014 | Yonce | A61N 1/378 607/66 |
| 2016/0206876 | A1* | 7/2016 | Rajguru | A61N 1/0456 |

OTHER PUBLICATIONS

DAKMED Inc Model 750 Peripheral Nerve Stimulator, Instructions and Specifications Jul. 1992 (4 pages).
Weisman et al., "Identification and Prediction of Diabetic Sensorimotor Polyneuropathy Using Individual and Simple Combinations of Nerve Conduction Study Parameters", PLOS One, Mar. 2013, vol. 8, Issue 3, e58783 (9 pages).
Texas Instruments, ADS1298ECG-FR/ADS1198ECG-FE, ECG Front-End Performance Demonstration Kit, User's Guide, May 2010, revised Sep. 2012, Literature Number: SBAU171C (65 pages).
Texas Instruments, TMS320C5515 Fixed-Point Digital Signal Processor, SPRS645F—Aug. 2010—Revised Oct. 2013 (159 pages).
Jin et al., "Can nerve conduction studies detect earlier and predict clinical diabetic neuropathy?", Journal of Diabetes Investigation, vol. 6, No. 1, 2015, pp. 18-20 (3 pages).

(Continued)

*Primary Examiner* — Nicole F Lavert
(74) *Attorney, Agent, or Firm* — Brian J. Pangrle (57) ABSTRACT

A wearable system can include at least one cuff; nerve activity acquisition electrodes; nerve stimulation electrodes; circuitry operatively coupled to the nerve activity acquisition electrodes and to the nerve stimulation electrodes; and memory operatively coupled to the circuitry that stores nerve information.

18 Claims, 11 Drawing Sheets

(56) References Cited

OTHER PUBLICATIONS

Texas Instruments, Low-Power, 8-Channel, 16-Bit Analog Front-End for Bipotential Measurements, ADS1194, ADS1196, ADS1198, SBAS471C—Apr. 2010—Revised Nov. 2011 (76 pages).
Texas Instruments, ADS129x Low-Power, 8-Channel, 24-Bit Analog Front-End for Biopotential Measurements, SBAS459K—Jan. 2010—Revised Aug. 2015 (107 pages).
Neurometrix Advance, FDA 510(k) Summary, 510(k) No. K070109, Apr. 25, 2008 (7 pages).
Neurometrix NC-STAT / DPN Check, User Manual, 2013, PN2203282 Rev G (21 pages).
XLTEK Neuropath, FDA 510(k) Summary, 510(k) No. K053058, Feb. 7, 2006 (3 pages).
NEUMED Inc., Brevio, Nerve Conduction Monitoring System, webpage, copyright 2001-2005 (1 page).
Blue Cross Blue Shield, Regence, Medical Policy Manual, Automated Point-of-Care Nerve Conduction Studies, Policy No. 128, Mar. 1, 2015 (12 pages).
Axon Industries, Axon II Neural Scanner, Medical Device Depot's Blog, Nov. 2, 2010 (1 page).
Michigan Neuropathy Screening Instrument (MNSI), 2000 (2 pages).
Cornblath, Diabetic Neuropathy: Diagnostic Methods: Adv Stud Med. 2004;4(8A):S650-S661 (12 pages).
Krause et al., Evaluation and Treatment of Diabetic Foot Ulcers, Clinical Diabetes, 24(2), 2006 pp. 91-93 (3 pages).

\* cited by examiner

NEUROSTIMULATION SYSTEM

RELATED APPLICATION

This application claims priority to and the benefit of a U.S. Provisional Application having Ser. No. 62/102,071, filed 11 Jan. 2016, which is incorporated by reference herein.

TECHNICAL FIELD

Subject matter disclosed herein generally relates to neurostimulation techniques and technologies.

BACKGROUND

Neurostimulation may be applied as a therapeutic type of stimulation, for example, where energy may be delivered to a body in a manner that activates tissue of the body.

COPYRIGHT NOTICE

A portion of the disclosure of this patent document contains material to which a claim for copyright is made. The copyright owner has no objection to the facsimile reproduction by anyone of the patent document or the patent disclosure, as it appears in the Patent and Trademark Office patent file or records, but reserves all other copyright rights whatsoever.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing general principles of the implementations. The scope of the described implementations should be ascertained with reference to the issued claims.

As an example, neurostimulation may be applied as a diagnostic type of stimulation that delivers energy to tissue, which may cause a nerve response (e.g., or responses of nerves) which may be measured, for example, as to attenuation. For example, neurostimulation may be applied to diagnose one or more aspects of conduction of by a nerve or nerves. As an example, measurements may be analyzed, for example, to determine status of a nerve or nerves, optionally via a model or models. As an example, an analysis can include receiving (e.g., accessing) information as to one or more predetermined limits, which may be, for example, indicative of healthy and/or diseased tissue. As an example, neurostimulation may be applied as a therapeutic type of stimulation, for example, where energy may be delivered to a body in a manner that activates tissue of the body (e.g., as part of a therapy). As an example, neurostimulation may be applied as a diagnostic type of stimulation and/or a therapeutic type of stimulation.

As an example, a system can include circuitry for nerve conduction monitoring and, for example, nerve stimulation. Such a system may include a wearable unit that may, for example, be wearable on a leg. For example, consider a boot-like unit that includes circuitry that can acquire information about a patient's leg and optionally deliver stimulation to the patient (e.g., at the leg and/or at one or more other places on the patient's body). As an example, a system may include a wearable unit that may, for example, be wearable on a hand. For example, consider a glove-like unit that includes circuitry that can acquire information about a patient's hand and optionally deliver stimulation to the patient (e.g., at the hand and/or at one or more other places on the patient's body).

As an example, a wearable device can include one or more cuffs. As an example, a cuff may be shaped and sized for a lower limb (e.g., lower leg, ankle, foot). As an example, a cuff may be shaped and sized for an upper limb (e.g., forearm, wrist, hand). As an example, a cuff may be part of a boot. As an example, a cuff may be part of a glove. As an example, in blood pressure monitoring, a blood pressure cuff may be used to encircle a portion of a body (e.g., an upper arm). As an example, in nerve monitoring, a cuff may be used to position electrodes and/or sensors with respect to tissue of a body (e.g., with respect to one or more nerves). As an example, a cuff may be used to carry equipment (e.g., one or more components of a nerve monitoring system, a nerve therapy system, a nerve monitoring and nerve therapy system, etc.). As an example, equipment can include one or more power supplies (e.g., one or more batteries, etc.).

As an example, a unit may include features for acquiring information as to one or more physiological processes (e.g., processes of the circulatory system, nervous system, etc.) and may include features for intervention (e.g., application/relief of pressure, stimulation, heat, etc.). As an example, a system may include a computer and/or mobile application for local and/or remote communication with a wearable unit. As an example, a system may include a cloud-based database for storage and analysis of data. As an example, a system may include one or more technical support services for remote testing, analysis support and reporting (e.g., service modules, etc.).

As an example, a system may include circuitry that can perform specialized Nerve Conduction Studies (NCS) for symptomatic diabetes patients. As an example, a system may be implemented for patients at risk for peripheral neuropathy (e.g., diabetes patients and especially pre-symptomatic diabetes patients). As an example, such a system may include one or more units that can monitor information about a diabetic patient or patients. In such an example, the system may make frequent assessments of peripheral nerves of the one or more patients, for example, to enable identification of future peripheral neuropathy in diabetes patients before they are symptomatic, providing objective data to assist in disease progression management; to facilitate use of a non-invasive device to monitor one or more patients for deterioration of nerve conduction function; to effectively and efficiently track therapeutic effectiveness for one or more patients with peripheral neuropathy.

While diabetes is mentioned as an example, a system may provide information as to one or more other conditions, alternatively and/or additionally. For example, consider a patient with an immune disease such as an autoimmune disease, a patient with exposure to one or more poisons/toxins (e.g., heavy metals or chemicals, etc.), a patient undergoing chemotherapy, a patient with a vitamin B deficiency, etc. As an example, a system may allow for monitoring neuro-toxic side-effects of chemotherapy and/or one or more other treatments (e.g., in an effort to minimize long-term damage, etc.).

As an example, a system may include a peripheral neuropathy monitoring device such as a Peripheral Neuropathy Monitoring Boot that can perform Nerve Conduction Studies (NCS) (e.g., home use, in a doctor's office, etc.). Such a boot may be relatively easy to use by patients, remotely accessible by healthcare professionals for Tele-Health services or on-going monitoring; testing frequency will be preassigned by health care professionals to enable nerve conduction velocity, amplitude, duration and latency datapoints to be frequently collected, stored and analyzed.

As an example, a boot can include fixed location electrodes and sensors in a wearable wraparound configuration that places electrodes for a nerve conduction test (e.g., a "neuroboot"). In such an example, locations may optionally be adjustable, for example, within a margin that may correspond to variations in human anatomy from human to human (e.g., leg to leg, etc.). As an example, a boot may be available in one or more sizes to accommodate variations in human anatomy. As an example, a method can include providing a boot that includes electrodes and sensors and placing the boot about a portion of a lower extremity (e.g., a portion of a lower leg, an ankle, a foot, etc.). As an example, such a method can include preparing electrodes and/or sensors prior to, during and/or after placement of the boot. While a boot is mentioned, as an example, a glove may be configured to include electrodes and sensors where such an arrangement of components can be utilized to perform nerve conduction tests where measured data may be analyzed to assess condition of one or more nerves that are disposed at least in part in a hand on which the glove is worn (e.g., a "neuroglove").

As an example, a wearable device that includes electrodes and sensors may be utilized to acquire data. As an example, a system may include, for example, a cloud database where data is stored and analyzed, and, for example, a computer application that enables communication between the device and database to enable Tele-Health services and remote access of data by healthcare professionals. For example, information acquired via one or more wearable devices may be transmitted via one or more networks, etc., to a remote location or remote locations.

As an example, a system may acquire and analyze data from NCS, for example, to create an individual patient's baseline and to trend and to compare information, for example, with one or more known and/or estimated thresholds for peripheral neuropathy. As an example, information for a plurality of subjects may be analyzed where, for example, such analysis may facilitate diagnosis and/or treatment of one or more conditions (e.g., for one or more of the subjects, one or more other subjects, etc.).

Diabetic sensorimotor polyneuropathy (DSP) is a common form of nerve injury in diabetes, with an estimated prevalence of 50%. It may involve motor, sensory, and autonomic nerves and may be characterized by a nerve impairment that is symmetrical and length-dependent. Such variable attributes of nerve injury and their manifestations can challenge diagnostic strategies for DSP. As an example, clinically relevant late stage complications of DSP may be predicted by one or more nerve parameters. In some instances, a single nerve parameter may be predictive for a patient or patients. Thus, NCS tends to be accepted as an objective test for the diagnosis of DSP and its sequelae.

An article by Weisman et al., entitled "Identification and Prediction of Diabetic Sensorimotor Polyneuropathy Using Individual and Simple Combinations of Nerve Conduction Study Parameters" PLoS ONE 8(3): e58783. doi:10.1371/journal.pone.0058783 is incorporated by reference herein. Weisman et al. evaluated diabetic sensorimotor polyneuropathy (DSP) and nerve conduction study (NCS) protocols as to predictive biomarkers. Weisman et al. aimed to determine the performance of single and simple combinations of NCS parameters for identification and future prediction of DSP. Weisman et al. includes data, which are analyzed to provide so-called normal values for individual NCS. For example, sural amplitude ≥7.2 microvolts age ≤65 and ≥5.5 microvolts for age >65, sural CV ≥40 m/s, peroneal amplitude ≥5 microvolts for age ≤65 and ≥3 mircovolts for age >65, peroneal CV ≥40 ms, peroneal F wave ≤59 ms for height ≥182.9 cm and ≤58 ms for height <182.9 cm, tibial amplitude ≥10 microvolts, tibial CV ≥40 m/s, tibial F wave ≤55 ms. As an example, a system may include such values, for example, stored in a data storage and/or stored locally in a wearable device and/or in a unit or units that can be operatively coupled to a wearable device (e.g., via wire and/or wirelessly), for example, for transmission of information to and/or from a unit or units to a wearable device (e.g., or wearable devices).

As an example, a system may include circuitry to monitor nerve activity. As an example, a system may include circuitry to monitor information about at least one nerve. As an example, a system may include circuitry to monitor information about multiple nerves, which may be different nerves. As an example, monitoring may include amplitude monitoring (e.g., for amplitude changes), waveform monitoring (e.g., for waveform duration changes, etc.), etc. As an example, a system may include marking one or more waveforms and optionally storing at least one marked waveform. As an example, a system may include circuitry that can monitor a single nerve at a plurality of locations along the nerve. As an example, a system may include circuitry that can monitor a plurality of nerves at at least one location. For example, two nerves may be proximate to each other at an anatomical location where a sensor (e.g., or sensors) may be positioned to acquire information from both of the nerves, optionally simultaneously and/or at different times.

As an example, a system may include one or more algorithms that may select from an array of electrodes (e.g., or arrays of electrodes), for example, to automatically get optimal electrode placement for optimal waveform for a patient. As an example, an electrode array may be characterized by geometry (e.g., a shape and arrangement of electrodes of the array). As an example, a wearable such as a boot may include one or more matrixed inflatable bladders, for example, to apply sufficient pressure on one or more emitting electrodes, sensors/detectors, etc. As an example, a boot may include one or more indexing features, matrixed bladders, elastic portions and VELCRO closures, etc. As an example, a portion of an ankle may provide for indexing (e.g., an anatomical marker, a fiducial, etc.). For example, consider an ankle bone that facilitates positioning of a wearable. As an example, equipment may include one or more electrode arrays that may optionally be passive or, for example, that may be active and operatively coupled to circuitry that may perform one or more functions such as filtering, amplification, etc. (e.g., consider circuitry integrated within an electrode array). As an example, one or more electrodes may be attached to a component such as, for example, a gel pad or, for example, a mechanism that may include fluid conduit(s) that can introduce gel to an electrode-skin interface (e.g., via pressure applied to a gel reservoir, etc.).

As an example, a system can include one or more algorithms for Disease Progression Monitoring (DPM). For example, consider algorithms to chart velocity, latency, duration and amplitude data with comparisons to normal ranges tailored over time by aggregating data by patient cohort, patient specific baseline and control limits.

As an example, a system can include circuitry for Remote Access (RA) such that, for example, waveforms and/or other data may be stored in a cloud database (e.g., and/or other type of database) and, for example, using the web and/or a mobile app (e.g., a unit that may execute an application where the unit is accessible by a patient and/or the patient's health-care provider for analysis and monitoring). As an example, connection to the Internet may provide an ability for real-time technical assistance/intervention as well as, for example, to update firmware in a seamless way (e.g., one or more settings, algorithms, etc.). As an example, a system may include modules for Data Pooling (DP). For example, consider data in a cloud database that can be aggregated and parsed for insights into baselines, thresholds and outcomes for different demographics As an example, a system may include one or more modules for Drug and Medical Device Development Support (e.g., a platform for peripheral neuropathy therapy development with the ability to upload specific clinical test protocols for pharmaceutical and device development clients).

As an example, a system may include a wearable with micro-machined sensors (e.g., one or more MEMS components, etc.). As an example, one or more "micro-machine" components may provide for monitoring blood flow and therefore catch vascular occlusions before they cause damage, provide for monitoring bone density, provide for body fat changes, etc. As an example, consider a capacitive micro-machined ultrasonic transducers (cMUTs) that can provide for portable ultrasound foot imaging to monitor for vascular occlusions, for example, to provide additional data for diabetic foot care. In such an example, the imaging may generate image data that can be stored, compressed, transmitted, analyzed, etc. As an example, a wearable may include on-board memory that can store one or more types of data. As an example, such data may be transmittable as raw and/or as processed data.

As an example, processed data can include data that is input to one or more algorithms implemented at least in part via instructions executable by a processor, which may be a microprocessor, microcontroller, etc. For example, consider an ARM-based and/or a RISC-based processor that may process data and output processed data, for example, to an interface for transmission, for storage, etc.

As an example, a system may include threshold values for peroneal conduction velocity and sural amplitude potential, for example, as best identified prevalent cases, with, for example, AROC 0.90 and 0.83, sensitivity 80 and 83%, specificity 89 and 72%, respectively. As an example, consider a baseline tibial F-wave latency, peroneal conduction velocity and the sum of three lower limb nerve conduction velocities (sural, peroneal, and tibial) that may provide a best predicted 4-year incidence (AROC 0.79, 0.79, and 0.85; sensitivity 79, 70 and 81%; specificity 63, 74 and 77%, respectively). As an example, a system may include one or more algorithms for determining trending of latency and conduction velocity (e.g., with or without secondary stimulating sites).

As an example, a system can include circuitry for measurement, trending and analysis of parameters to flag changes, for example, early enough so intervention can either slow the progression of peripheral neuropathy in pre-symptomatic patients or assist in therapy modulation in patients undergoing therapy for prevalent peripheral neuropathy.

As an example, a system can include circuitry for pre-symptomatic and/or post-symptomatic diagnostics, for example, consider nerve conduction monitoring for preemptive detection of nerve function degeneration, detect peripheral neuropathy disease progression earlier than the current standard of care, monitor therapy effectiveness for patients being treated for peripheral neuropathy (e.g., to offer a cost-effective monitoring process for peripheral neuropathy therapeutic research).

As an example, a system may allow for neurology labs to test more patients by reducing the testing and report generation time (e.g., to under 10 min) and to provide an ability for patients to self-monitor (e.g., optionally including Tele-Health).

As an example, a system may be implemented for pain management, optionally in combination with one or more other functions. For example, consider pain reduction by electrical stimulation, which may act to improve quality of life and reduce cost of pain management in peripheral neuropathy. As an example, a system may provide for diagnosis and treatment of one or more neuropathy conditions. As an example, a method may include one or more of managing pain, controlling blood glucose using a topical drug regimen, etc., for example, with outcomes being monitored (e.g., by a wearable system that may be operatively coupled to a communication network).

As an example, a wearable may include indexing features such as a heel cup, ankle bone locator, strap between first and second toe, etc. As an example, a wearable may include electrode arrays and temperature and pressure sensors marking (e.g., to facilitate positioning). As an example, a wearable may include one or more bladder systems or other types of systems to apply pressure, as appropriate, for data acquisition, stimulation, etc. As an example, a fastening system of a wearable may include materials such as VELCRO or other types of materials.

As an example, a wearable may optionally include different diameter electrodes. As an example, a stimulation electrode or electrodes may be indexed to one or more anatomical markers (e.g., ankle, etc.) and appropriately matched electrodes (e.g., anode and cathode placed a desired distance apart such as a couple of centimeters, etc.). As an example, recording electrodes may be disposed a distance from stimulation electrodes (e.g., to improve signal to noise ratio, etc.). As an example, a distance of about 10 centimeters may be used between recording and stimulation electrodes (e.g., which may be fixed via configuration of electrodes of a wearable). As an example, appropriately matched recording electrodes (e.g., active and reference) may be at a distance of about 2 cm apart) within an arrays. As an example, testing may determine a stimulating location (e.g., where testing can see which electrode pairs, etc. provide desired results). As an example, electrodes arrays may be integrated into a wearable.

As an example, parameters that may be indicators can include Amplitude (e.g., Sural Amp (µV), Peroneal Amp (mV), Tibial Amp (mV), Plantar Amp (µV), Sum of Amp, etc.); and/or duration of waveforms. As an example, waveforms may be marked and measured, mean, SD, min and max values determined. As an example, parameters may include, duration, latency and Conduction Velocity (CV) (e.g., and optionally one or more other parameters).

Figure 1:
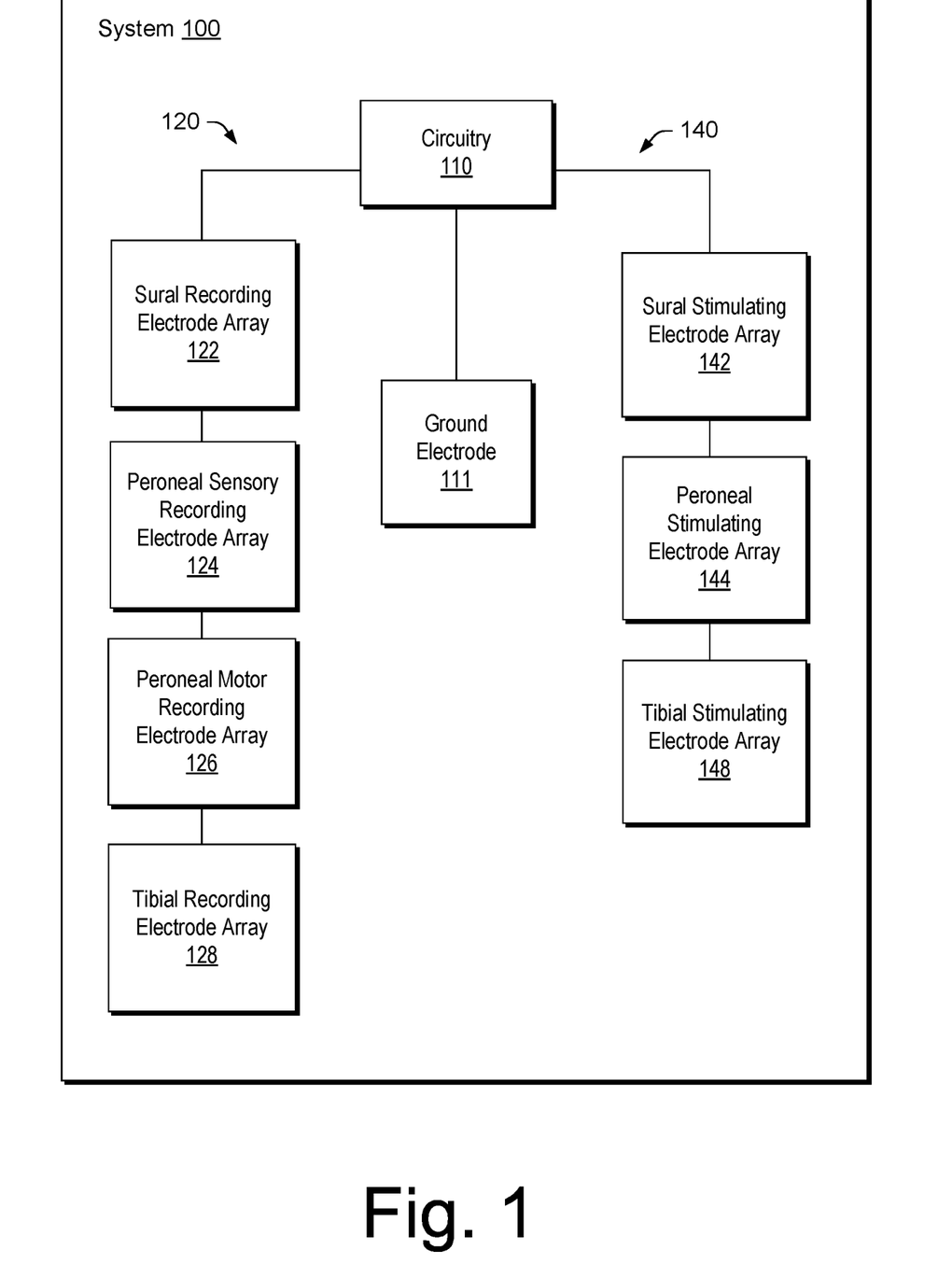
FIG. 1 illustrates an example of a system.

FIG. 1 illustrates an example of a system 100. As shown, the system 100 includes circuitry 110 operatively coupled to a ground electrode 111, a data acquisition bus 120 and a stimulation bus 140. The data acquisition bus 120 may include one or more components operatively coupled thereto for purposes of acquiring data, for example, consider a sural recording electrode array 122, a peroneal sensory recording electrode array 124, a peroneal motor recording electrode array 126, and a tibial recording electrode array 128. The stimulation bus 140 may include one or more components operatively coupled thereto for purposes of delivery of energy that can stimulate tissue, for example, consider a sural stimulating electrode array 142, a peroneal stimulating electrode array 144, and a tibial stimulating electrode array 148. As an example, the circuitry 110 may acquire information and then control stimulation based at least in part on the acquired information. As an example, the circuitry 110 may acquire information, which may be stored, analyzed, communicated, etc. As an example, information acquired may include one or more of information as to nerve conduction, temperature, blood glucose levels, BMI, etc.

Figure 2:
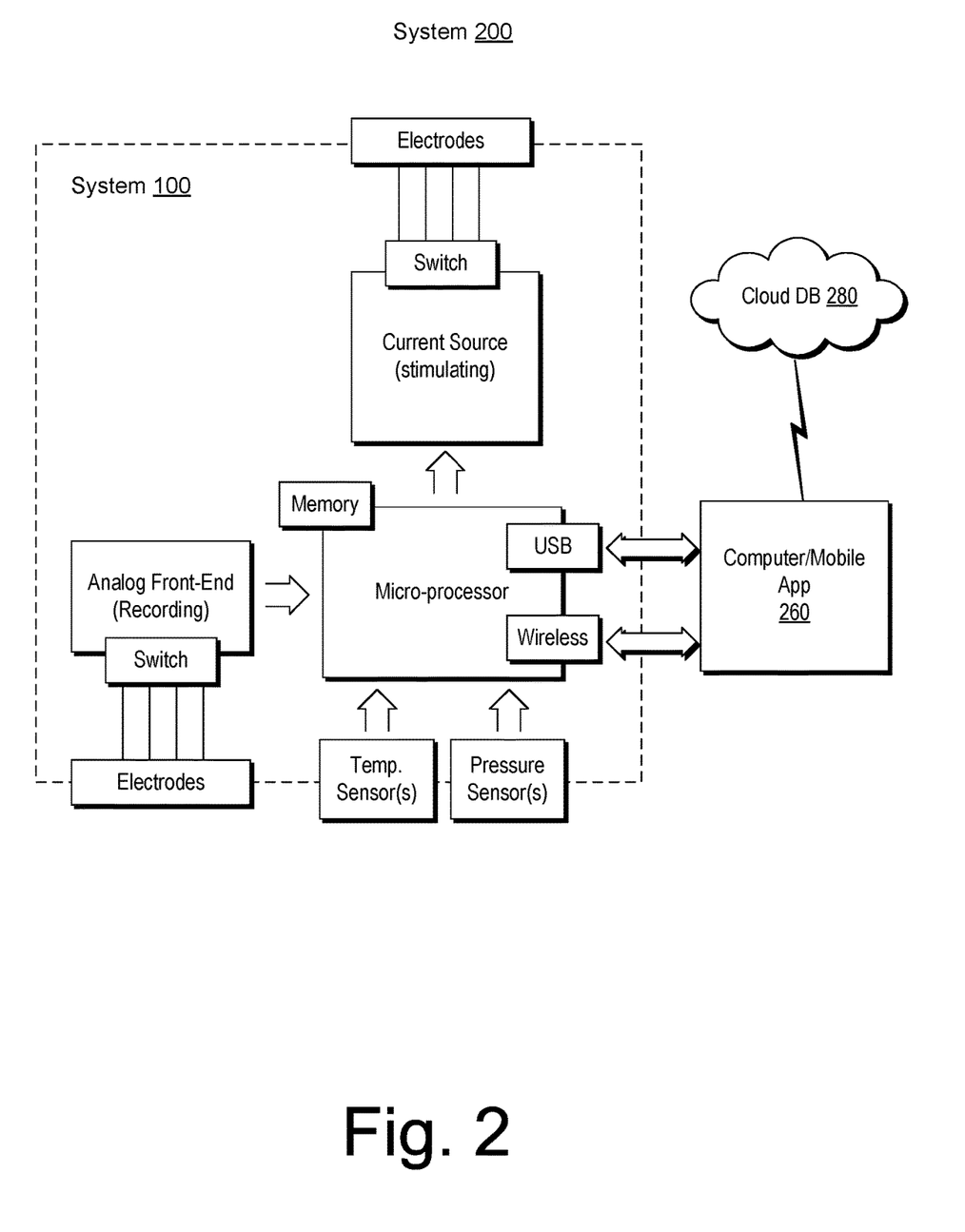
FIG. 2 illustrates an example of a system.

FIG. 2 illustrates an example of a system 200 that includes an example of the system 100, with various components illustrated therein. For example, the circuitry 110 may include a micro-processor with interfaces such as a USB interface, a wireless interface, sensor interfaces (e.g., for temperature sensors, pressure sensors, etc.), etc. As shown, the system 100 may include an analog front-end, optionally with switch circuitry, operatively coupled to electrodes and the system 100 may include current source circuitry, optionally with switch circuitry, operatively coupled to electrodes. As an example, the micro-processor may acquire information from one or more components (e.g., electrodes, sensors, etc.) and deliver stimulation energy based at least in part on such information. As shown in FIG. 2, the system 200 includes an application 260 (e.g., a computer application, a mobile application, etc.) that may be executed on a platform or platforms (e.g., a computing platform) that includes an interface or interfaces for accessing remote information. For example, consider a cloud-based database 280 as a source of remote information and/or as a storage that can receive information from the application 260 for storage therein. As an example, the application 260 may be upgradable via the one or more interfaces. As shown, one or more interfaces of the micro-processor of the system 100 may communicate with the application 260, for example, via wire and/or wirelessly (e.g., consider WIFI, BLUETOOTH, etc.).

Figure 3:
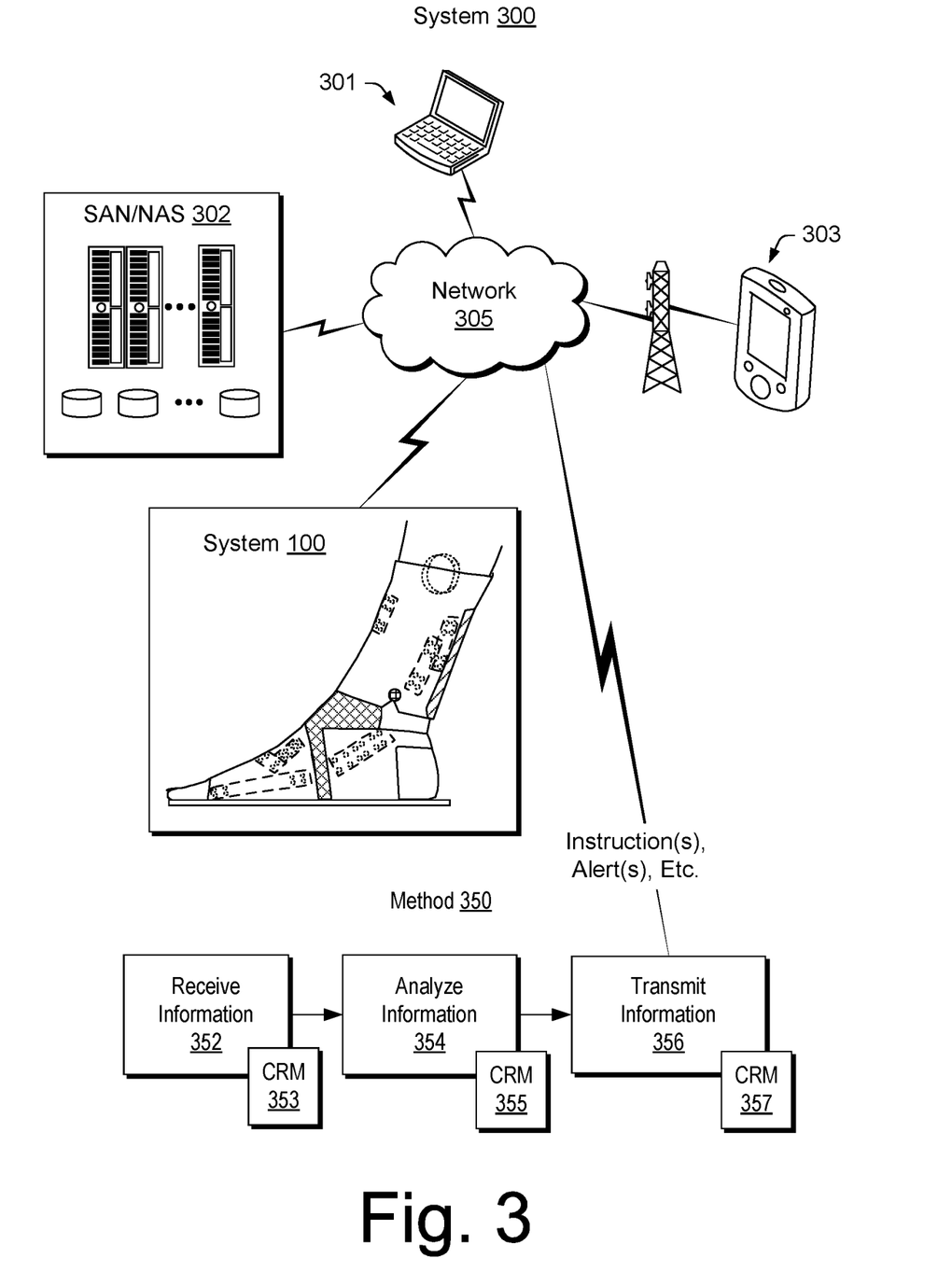
FIG. 3 illustrates an example of a system and an example of a method.

FIG. 3 illustrates an example of a system 300 and an example of a method 350. As shown, the system includes a computing device 301, a computing device 303, a storage 302, and a network 305. An example of the system 100 is also shown as being operatively coupled to the network 305. For example, circuitry of the system 100 may include one or more interfaces that can communicate with the network 305 and hence, for example, one or more of the computing device 301, the computing device 303 and the storage 302.

As an example, one or more of the components of the system may be configured to perform a method such as, for example, the method 350. As shown, the method 350 includes a reception block 352 for receiving information, an analysis block 354 for analyzing information and a transmission block 356 for transmitting information. Also shown are computer-readable storage media (CRM) that may include processor-executable instructions to perform one or more actions of the method 350. As an example, consider one or more storage media that are non-transitory and not a carrier wave. As an example, the transmission block 356 may transmit information via the network 305 (e.g., to one or more of the components). As an example, the reception block 352 may receive information from one or more components of the system 300, which is shown as including the system 100.

Figure 4:
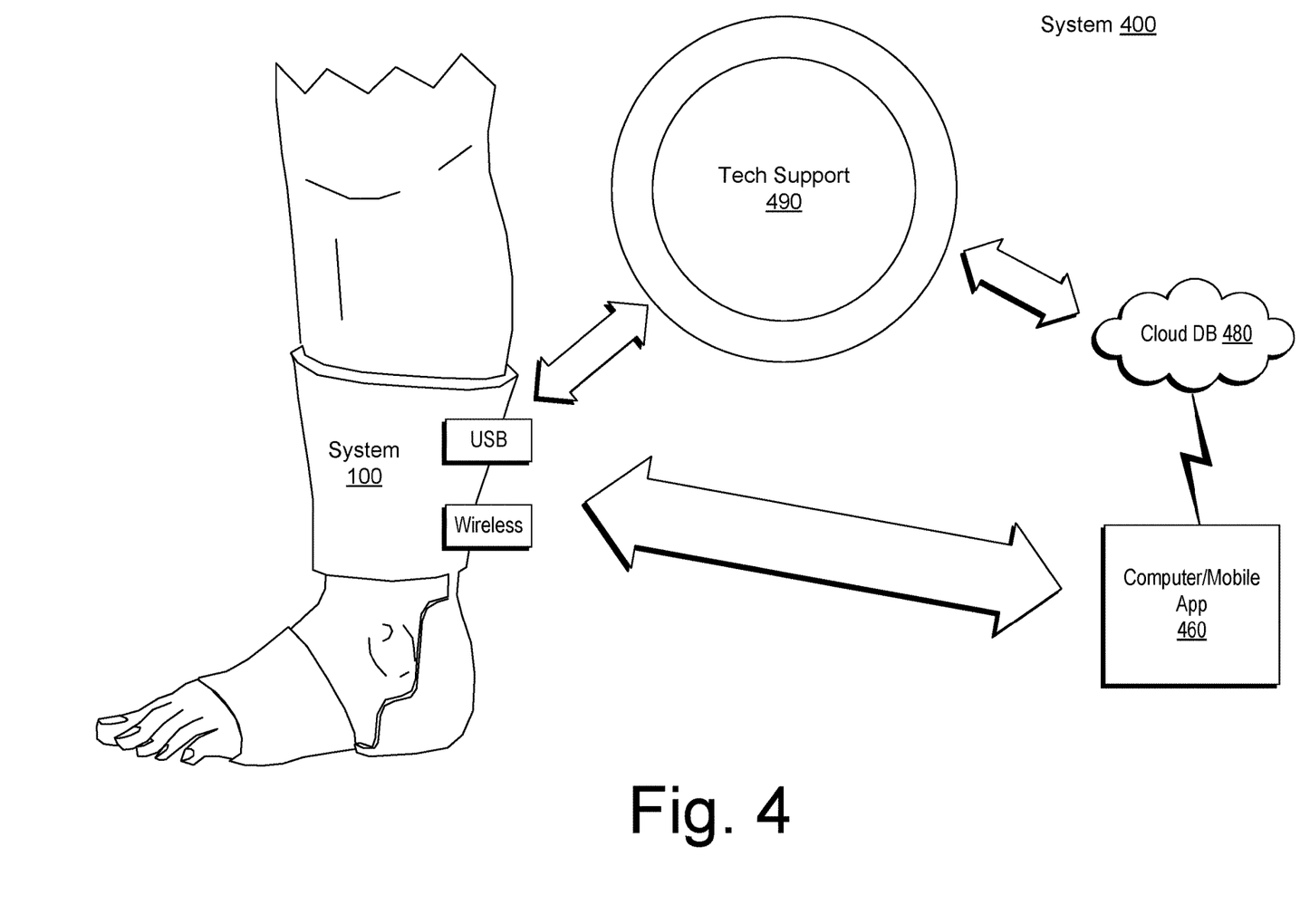
FIG. 4 illustrates an example of a system.

FIG. 4 illustrates an example of a system 400 that includes an example of the system 100 along with an example of an application 460, an example of a cloud-based database 480 and an example of a technical support module or modules 490. For example, the technical support module or modules 490 may be associated with operators that can assess, maintain, manage, etc. the system 100.

Figure 5:
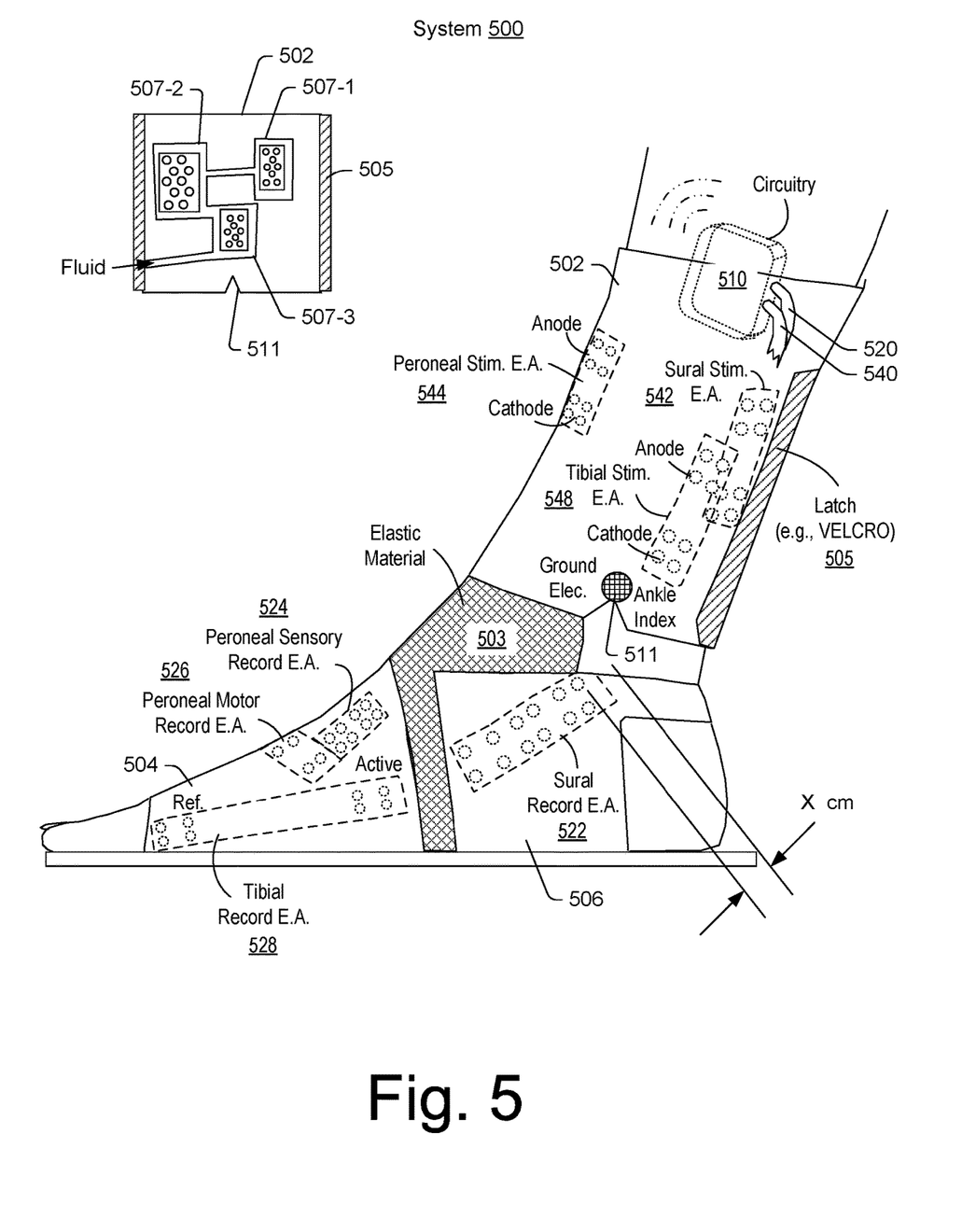
FIG. 5 illustrates an example of a system.

FIG. 5 illustrates an example of a system 500, which may be an example of a particular embodiment of the system 100. As shown, the system 500 includes a shin cuff 502 that includes various electrode arrays, a latching mechanism 505 (e.g., VELCRO, etc.) and, for example, one or more matrixed bladders 507-1, 507-2 and 507-3 that can be fluid pressurized to pressure electrodes against skin. For example, consider gas as a fluid or liquid as a fluid that may be adjusted as to pressure to cause a bladder to fill or empty to varying degree to achieve desired force of electrodes against skin (e.g., epidermis). As shown, the shin cuff 502 includes an index 511, which may be a notch, etc. to facilitate locating and positioning of the shin cuff 502 with respect to an ankle bone (e.g., part of the tibia and/or part of the fibula).

As an example, an electrode array may be fabricated from conductive materials set in an insulator (e.g., flex board material). As an example, matrixed air bladders may be used to apply pressure to one or more electrode arrays.

As shown, the system 500 can include elastic material 503, a foot cuff 504 and a heel cuff 506 where, for example, the elastic material 503 is operatively coupled to the shin cuff 502, the foot cuff 504 and the heel cuff 506.

As to electrodes, the system 500 includes various electrodes, which are labeled 522, 524, 526, 528, 542, 544 and 548 (see also FIG. 1). The system 500 includes circuitry 510 that includes a bus 520 and a bus 540, which may be an acquisition bus and a stimulation bus, respectively. As an example, electrode arrays may include cathode and anode electrodes. As an example, the dimension "X" in FIG. 5 may be about 2 cm. As an example, the system 500 can include one or more power sources. For example, the system 500 can include one or more batteries (e.g., operatively coupled to circuitry). As an example, a battery may be a lithium-ion based battery. As an example, a battery may provide power sufficient for delivery of energy to tissue to stimulate one or more nerves. As an example, a system can include one or more power systems, for example, consider a power system for delivering energy to tissue and a power system for operating circuitry. In such an example, the system may include a power source for delivery of energy and include another power source for operating circuitry such as control circuitry (e.g., to control stimulation, to control acquisition, to control data analysis, etc.).

Figure 6:
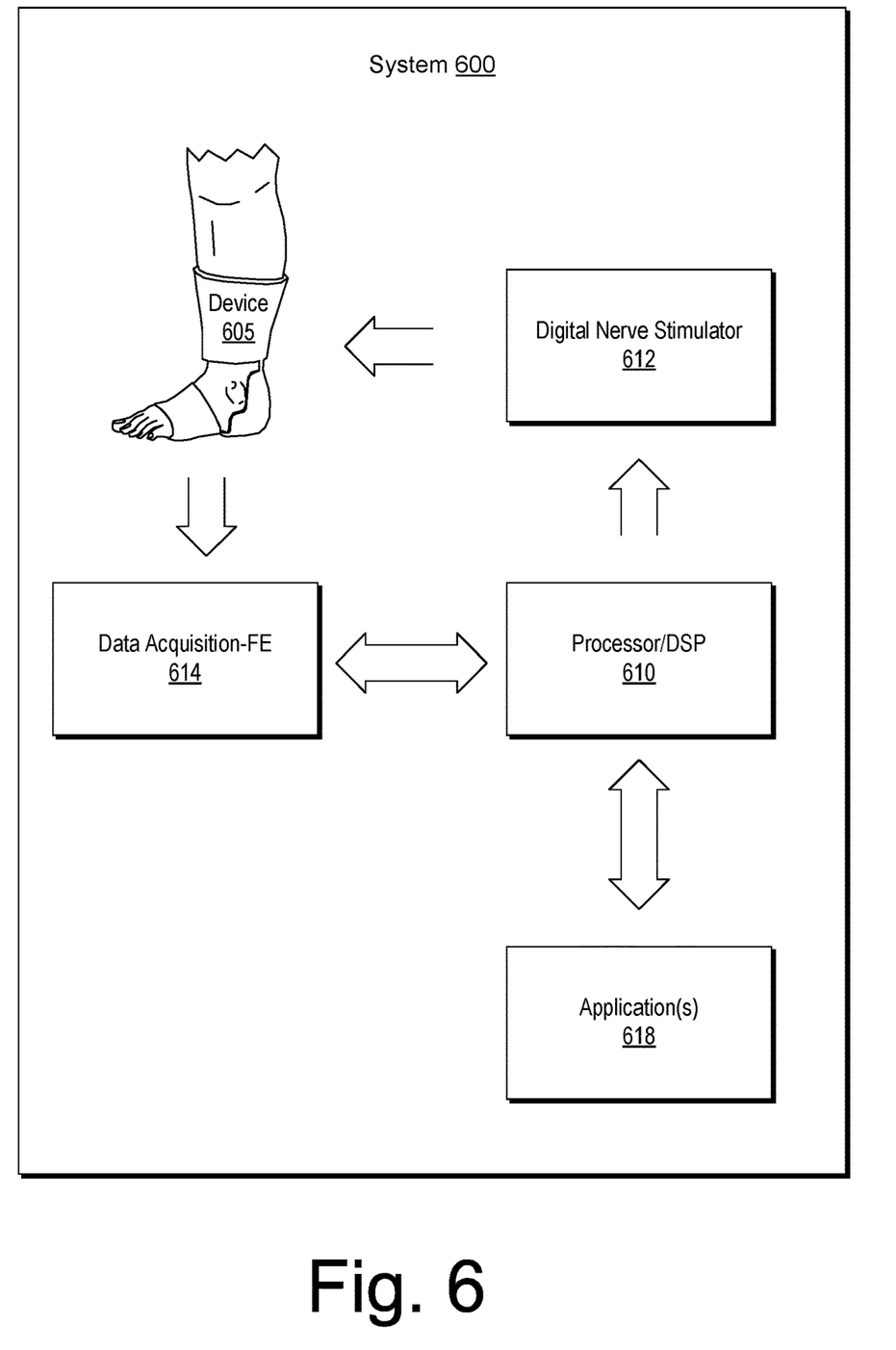
FIG. 6 illustrates an example of a system.

FIG. 6 illustrates an example of a system 600 that includes a device 605, a processor (e.g., DSP, etc.) 610, a digital nerve stimulator 612, a data acquisition front-end 614 and one or more applications 618. As an example, such components may include circuitry such as, for example, circuitry as in one or more of a C5515 EVM processor/DSP (Texas Instruments), a DAKMED 750 digital nerve stimulator, an ADS1298ECG-FE (Texas Instruments), etc.

Figure 7:
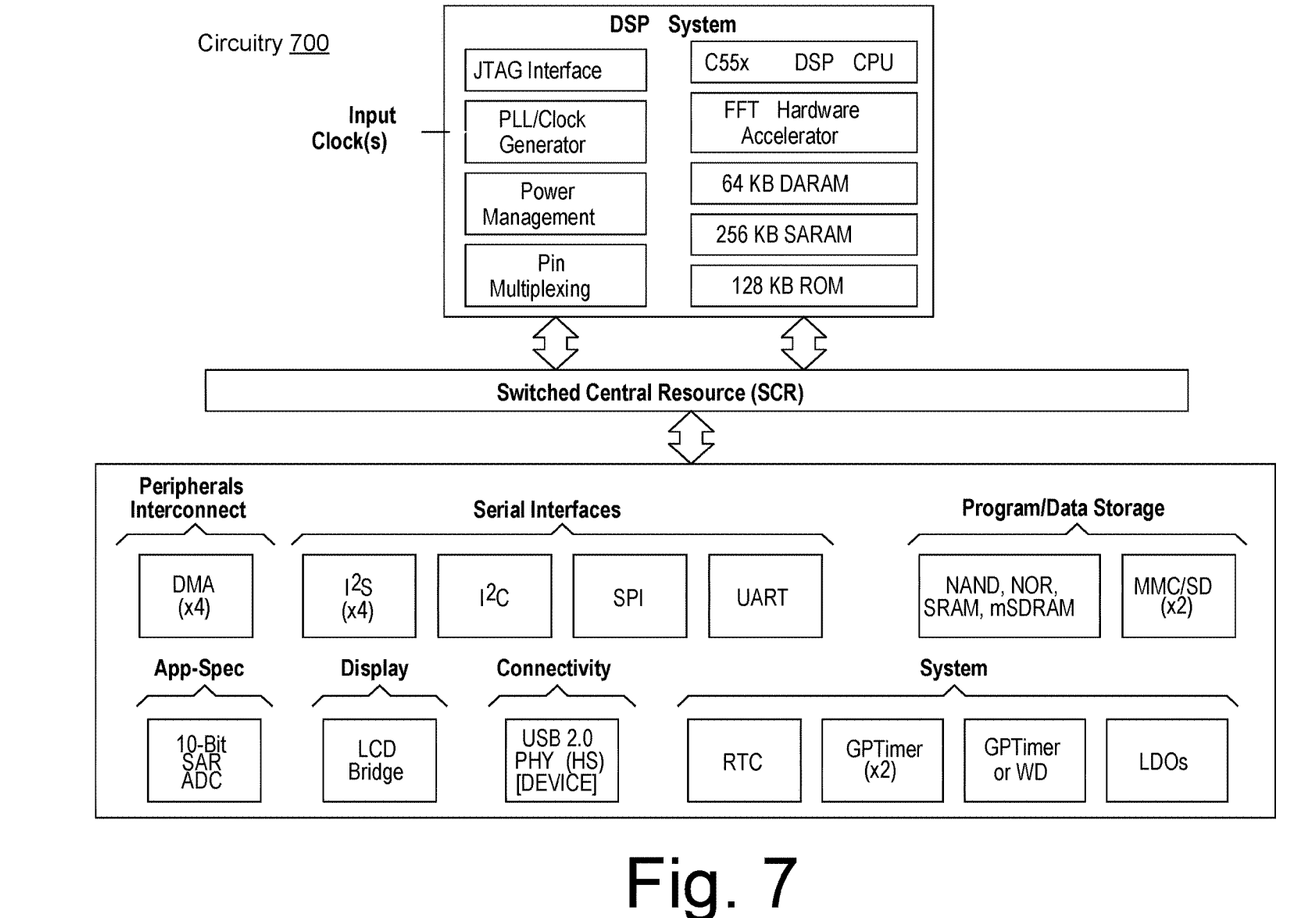
FIG. 7 illustrates examples of circuitry.

FIG. 7 illustrates examples of circuitry 700. As an example, the circuitry 700 may include processor/DSP circuitry such as that of a C5515 EVM of Texas Instruments.

Figure 8:
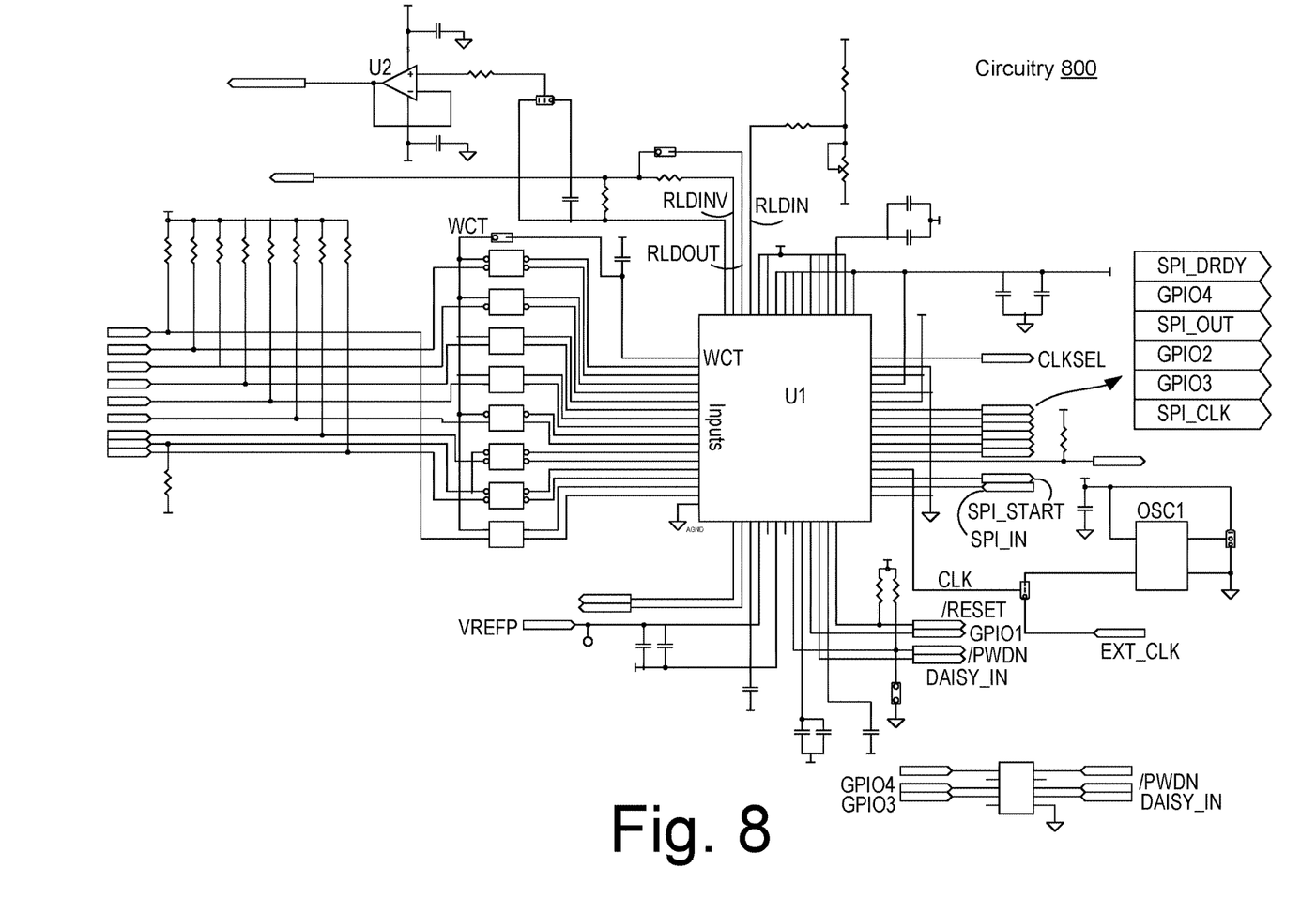
FIG. 8 illustrates examples of circuitry.

FIG. 8 illustrates examples of circuitry 800. As an example, the circuitry 800 may include processor/DSP circuitry such as that of, for example, an ADS1298ECG-FE of Texas Instruments (e.g., or other circuitry).

Figure 9:
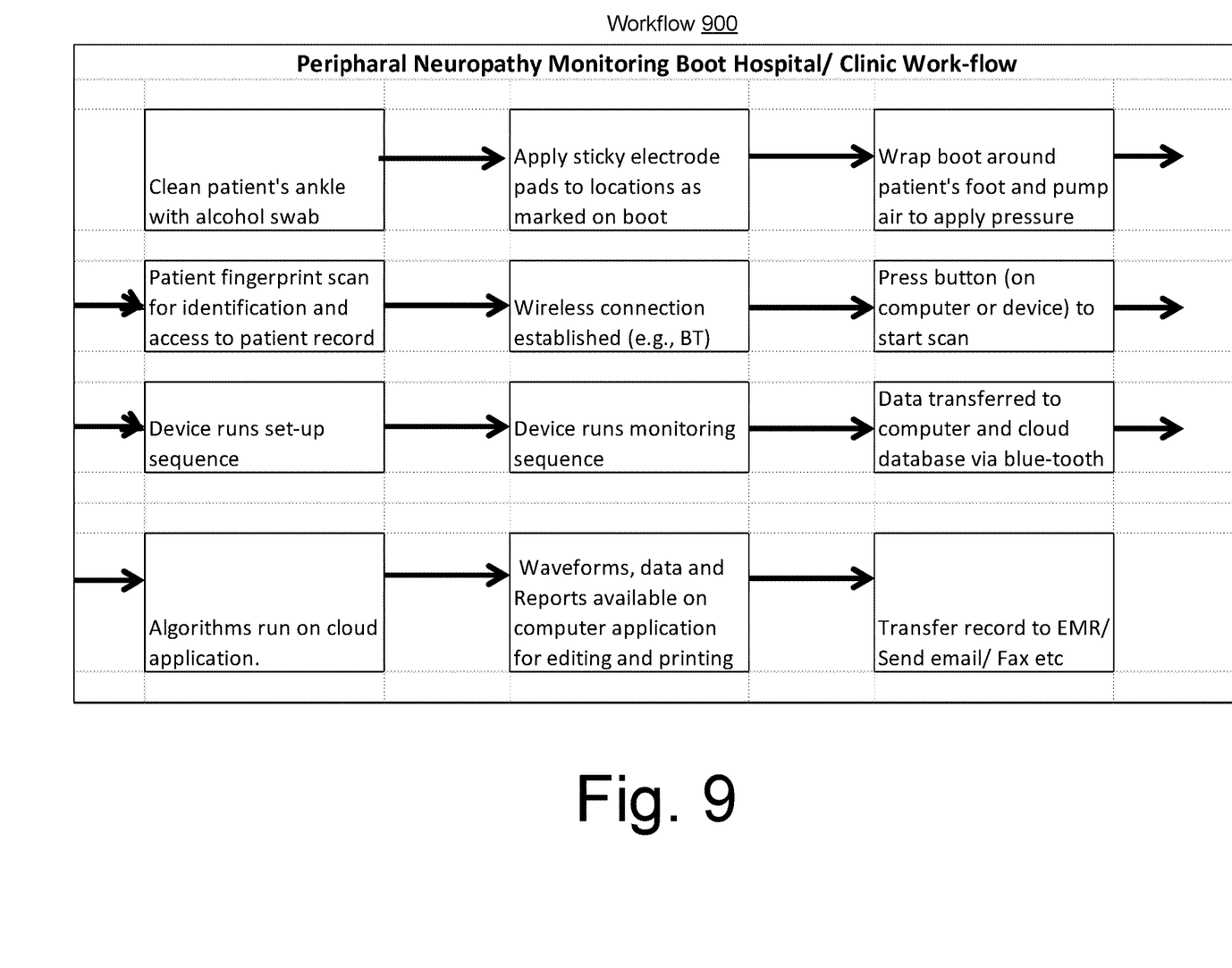
FIG. 9 illustrates an example of a workflow.

FIG. 9 illustrates an example of a workflow 900 associated with an example scenario.

Figure 10:
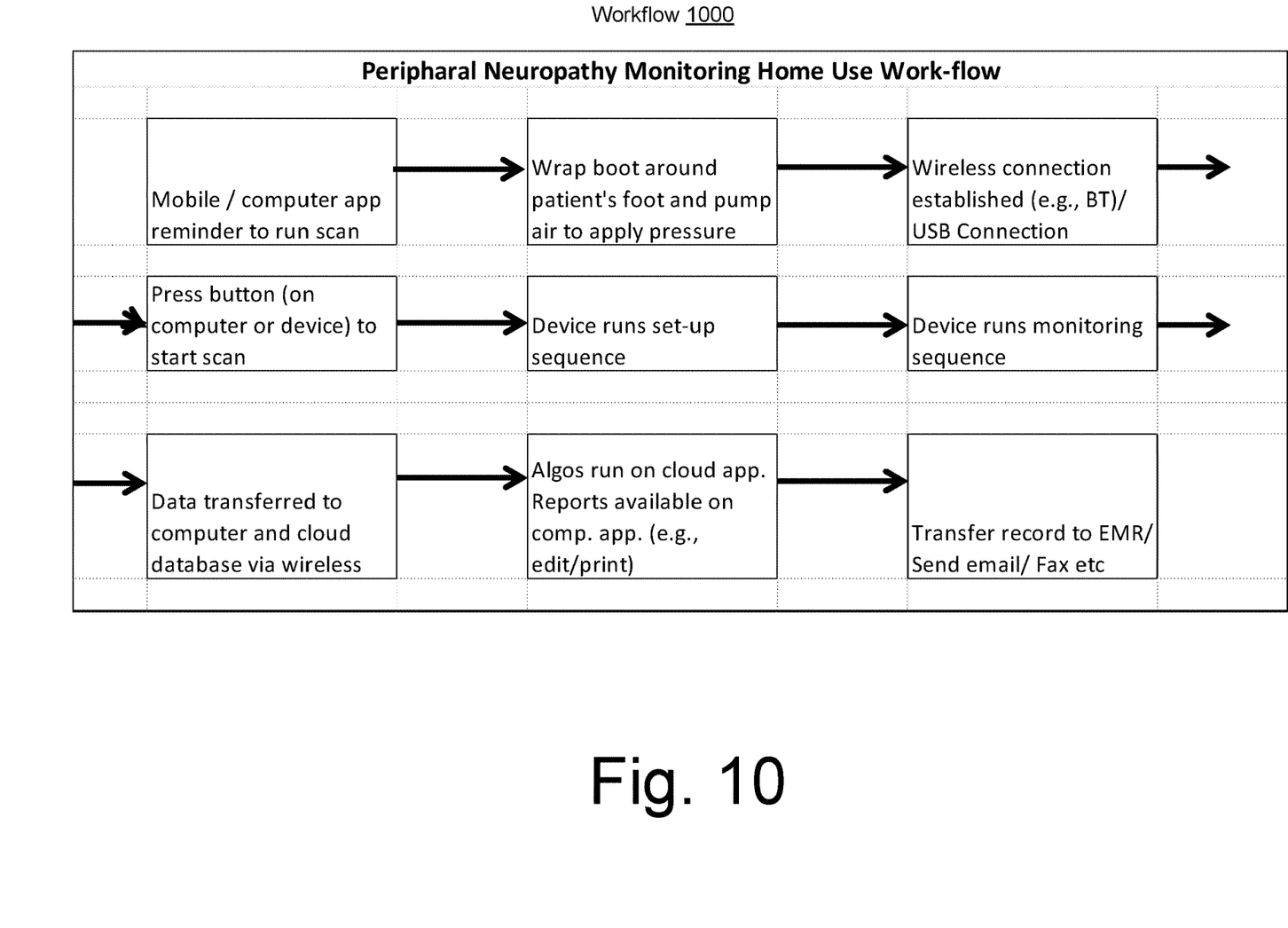
FIG. 10 illustrates an example of a workflow.

FIG. 10 illustrates an example of a workflow 1000 associated with an example scenario.

Figure 11:
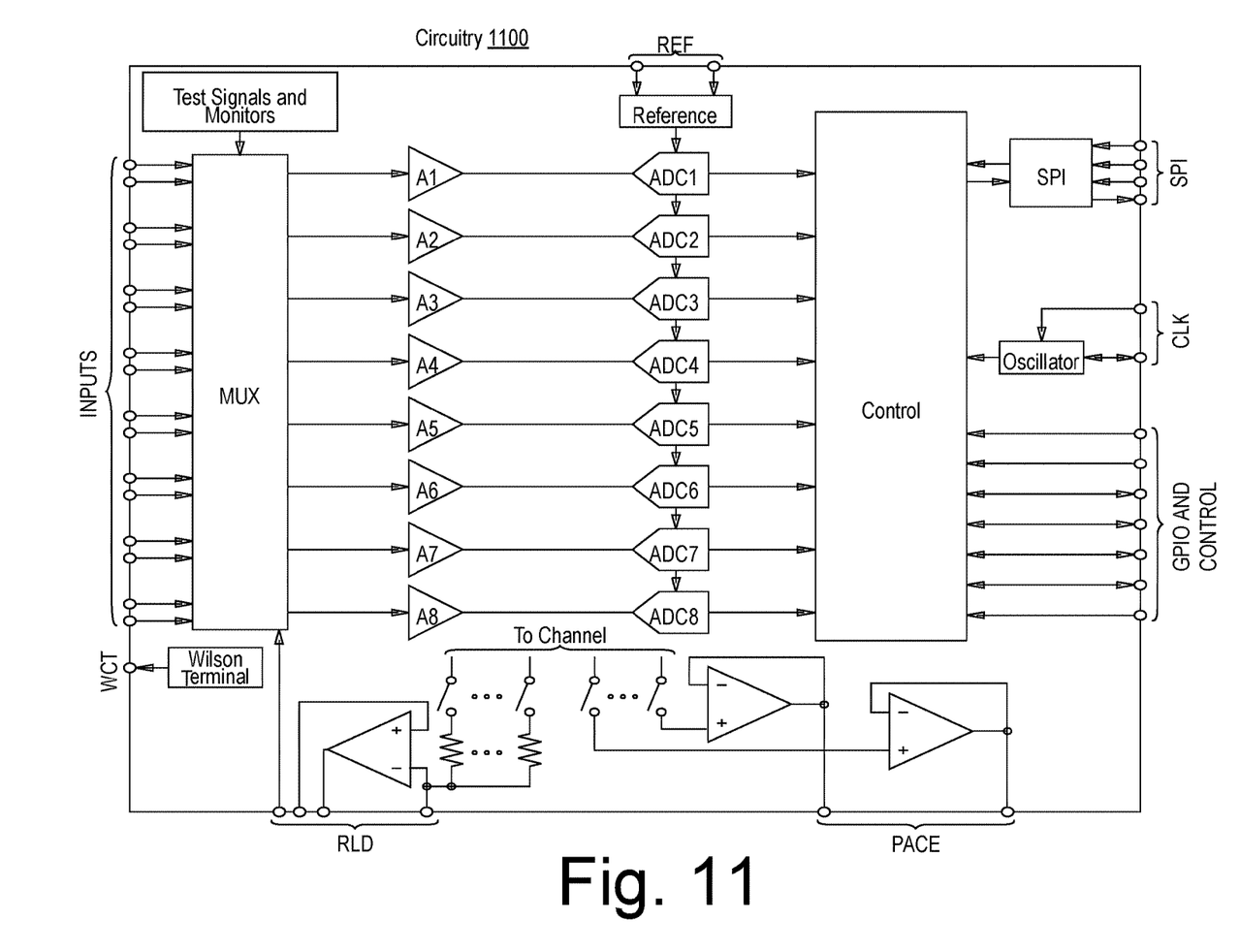
FIG. 11 illustrates an example of circuitry.

FIG. 11 illustrates an example of a schematic 1100. As an example, one or more features of the schematic 1100 may be included in the circuitry of FIG. 8.

As an example, a system can include a multichannel, simultaneous sampling, 16-bit, delta-sigma ($\Delta\Sigma$) analog-to-digital converters (ADCs) with a built-in programmable gain amplifier (PGA), internal reference, and an onboard oscillator.

As an example, a system can include a multichannel, simultaneous sampling, 24-bit, delta-sigma ($\Delta\Sigma$) analog-to-digital converters (ADCs) with built-in programmable gain amplifiers (PGAs), internal reference, and an onboard oscillator.

As an example, a system can include a flexible input multiplexer (mux) per channel that can be independently connected to internally-generated signals, for example, for one or more of test, temperature, and lead-off detection. As an example, one or more types of configurations of input channel(s) may be selected for derivation of an output signal or signals. As an example, a system may operate at data rates of the order of about 32 kSPS (e.g., or more or less).

As an example, a system can include integrated amplifiers that generate a Wilson central terminal (WCT) and, for example, one or more Goldberger central terminals (GCT) (e.g., as may be utilized in a standard 12-lead ECG). As an example, various circuits may be cascaded in a high channel count system, for example, in a daisy-chain configuration. As an example, a package of a circuit may be of the order of mm×mm (e.g., consider 8-mm×8-mm, with 64-ball BGA, and a TQFP-64, etc.). As an example, a system may be suitable for operation over a range of temperatures (e.g., 0° C. to 70° C., −40° C. to +85° C., etc.).

As an example, a system may include one or more algorithms to cycle through available stimulating and recording electrode pairs and select those that provide the best test capability.

As an example, a system may include circuitry for performing waveform analysis. As an example, a system may include one or more algorithms to mark and measure inflection points, amplitude, duration of waveform, latency (time between stimulation and response corrected for any action potential), conduction velocity (nerve distance traveled by electrical pulse divided by latency), etc.

As an example, a method can include measuring distance traveled by an electrical pulse or electrical pulses (e.g., via fixed anatomically correct paths scribed on a "boot", a "glove", etc.).

As an example, a system can include acquisition electrodes, stimulation electrodes and circuitry operatively coupled to the data acquisition electrodes and to the stimulation electrodes. Such a system may include one or more wearable components. As an example, consider one or more of a shin cuff, a foot cuff, a heel cuff, etc. As an example, a system may be wearable and include at least one pressurizable bladder.

As an example, a wearable device may include one or more individual electrodes and/or one or more arrays of electrodes. As an example, an electrode may be "passive" or, for example, "active". As an example, an electrode or electrodes may be operatively coupled to circuitry (e.g., for filtering, amplification, stimulation, etc.). As an example, a wearable device may include a mechanism to dispense gel (e.g., for coupling skin and electrode surfaces). As an example, a wearable device may include one or more gel pads.

As an example, a wearable device may include one or more sensors. As an example, a sensor may be a pressure sensor (e.g., strain gauge, etc.), a temperature sensor (e.g., thermocouple, etc.), a circulation sensor (e.g., light-based emitter and detector, etc.), a blood glucose monitoring sensor, a BMI sensor (e.g., using conduction, resistance, impedance, etc.), or another type of sensor that may acquire information germane to one or more physiological conditions, environmental conditions, activity of a patient, etc.

As an example, a system may be housed in a rigid material for structural integrity. As an example, a system may be customized to a particular patient. As an example, a method of manufacture may include scanning a body part (e.g., a lower portion of a leg, etc. via a 3D scanner) and then manufacturing one or more components that may enable custom-fitting of a wearable to a patient.

As an example, a system may include one or more temperature sensors (e.g., direct and/or indirect) and may include a mechanism that can control temperature, for example, in an effort to maintain temperature within a desired temperature range (e.g., before performing particular types of data acquisition, etc.). As an example, a method may aim to correct for temperature (e.g., for purposes of data comparisons, etc.).

As an example, a wearable system can include at least one cuff; nerve activity acquisition electrodes; nerve stimulation electrodes; circuitry operatively coupled to the nerve activity acquisition electrodes and to the nerve stimulation electrodes; and memory operatively coupled to the circuitry that stores nerve information. In such an example, the nerve information can include information indicative of nerve activity amplitudes. As an example, amplitudes with respect to time may be waveforms. As an example, a wearable system may acquire nerve information that includes information indicative of nerve activity waveforms.

As an example, a wearable system can include at least one cuff is, for example, a shin cuff, a foot cuff, an ankle cuff or a heel cuff. As an example, a wearable system can include at least one cuff that is, for example, a palm cuff or a wrist cuff.

As an example, a wearable system can include at least one pressurizable bladder. In such an example, the at least one pressurizable bladder may be operatively coupled to a pressurization unit controllable via the circuitry. For example, consider circuitry that can trigger pressurization at a time appropriate for performing stimulation, sensing, etc. As an example, circuitry may operate according to a schedule where pressurization occurs followed by an action such as, for example, delivery of energy to tissue, sensing of energy associated with tissue, etc.

As an example, a wearable system can include a boot. As an example, wearable system can include a glove.

As an example, a method can include receiving nerve information from a wearable system that includes at least one cuff, nerve activity acquisition electrodes, nerve stimulation electrodes, circuitry operatively coupled to the nerve activity acquisition electrodes and to the nerve stimulation electrodes, and memory operatively coupled to the circuitry that stores the nerve information; analyzing at least a portion of the nerve information; and, based at least in part on the analyzing, operating the wearable system.

As an example, an analysis may aim to determine quality of measured signals. For example, where a signal may be low in amplitude, a wearable system may repeat one or more actions. In such an example, consider an action such as adjusting a stimulation energy, adjusting a gain for sensing nerve activity, adjusting a pressurizable bladder to increase contact force between skin and one or more electrodes. As an example, a wearable system may determine a frequency of stimulation and acquisition based at least in part on analyzing nerve information. As an example, a wearable system may determine whether or not to transmit information based at least in part on analyzing. For example, operating a wearable system based at least in part on analyzing can include issuing an alert where, for example, the alert may be indicative of a condition associated with nerve conduction (e.g., a nerve conduction diagnosis, etc.). As an example, an operation of a wearable system can be an optimization operation, for example, to optimize an arrangement of electrodes, for example, for delivery of stimulation energy to tissue and/or for sensing of energy (e.g., tissue response to delivery of stimulation energy, etc.). For example, operating a wearable system can include selecting an electrode arrangement, for example, for use in delivery of energy to tissue or, for example, for use in sensing nerve activity, etc.

As an example, analyzing can include determining at least one value of at least one operational parameter of a wearable system. As an example, analyzing can include analyzing at least a portion of nerve information for peripheral neuropathy. As an example, analyzing can include analyzing at least a portion of nerve information for nerve conduction of at least one nerve. As an example, analyzing can include analyzing at least a portion of nerve information for nerve conduction of at least two nerves.

As an example, a method can include analyzing velocity of nerve conduction. As an example, a method can include analyzing latency of nerve conduction. As an example, a method can include analyzing amplitude of nerve conduction. As an example, a method can include analyzing duration of at least one nerve conduction waveform. As an example, a method can analyzing changes with respect to time, for example, of one or more of latency, conduction velocity, amplitude and duration.

As an example, analyzing can include determining whether one or more parameter values are in an acceptable range or in range indicative of neuropathy. For example, consider comparing acquired information (e.g., raw and/or analyzed) to one or more predetermined values.

As an example, a method can include, for each of a plurality of nerve stimulation electrode arrangements, delivering energy to tissue; for each of a plurality of nerve recording electrode arrangements, sensing nerve responses to delivered energy; based at least in part on the responses, selecting an optimal one of the nerve stimulation electrode arrangements and selecting an optimal one of the nerve recording electrode arrangements; and operating a wearable neurostimulation device using the optimal one of the nerve stimulation electrode arrangements and using the optimal one of the nerve recording electrode arrangements. In such an example, operating can include acquiring nerve conduction information.

As an example, a method can be a setup method. For example, consider a method where energy delivered is cycled through various available nerve stimulation electrodes, for example, to select the best available stimulation location. As an example, a method can include, analyzing the ability to record energy transmitted through nerve, cycled through various available recording electrodes, for example, to select the best available recording location.

Although various examples of methods, devices, systems, designs, etc., have been described in language specific to structural features and/or methodological acts, it is to be understood that the subject matter defined in the appended claims is not necessarily limited to the specific features or acts described. Rather, the specific features and acts are disclosed as examples of forms of implementing the claimed methods, devices, systems, designs, etc.

What is claimed is:

1. A non-invasive wearable system comprising:
at least one lower leg cuff;
nerve activity acquisition electrodes that selectably define a plurality of different acquisition arrays;
nerve stimulation electrodes that selectably define a plurality of different stimulation arrays;
circuitry operatively coupled to the nerve activity acquisition electrodes and to the nerve stimulation electrodes;
memory;
circuitry that, for each of the plurality of different stimulation arrays, delivers energy to tissue;
circuitry that, for each of the plurality of different acquisition arrays, senses nerve responses to delivered energy;
circuitry that, based at least in part on the responses, selects an optimal one of the plurality of different stimulation arrays and selects an optimal one of the plurality of different acquisition arrays;
circuitry that operates the non-invasive wearable system using the optimal one of the plurality of different stimulation arrays and using the optimal one of the plurality of different acquisition arrays;
circuitry that, during operation of the non-invasive wearable system, acquires nerve conduction information; and
circuitry that stores the nerve conduction information to the memory.

2. The wearable system of claim 1 wherein the nerve conduction information comprises information indicative of nerve activity amplitudes.

3. The wearable system of claim 1 wherein the at least one lower leg cuff comprises a shin cuff and a foot cuff.

4. The wearable system of claim 1 comprising at least one pressurizable bladder.

5. The wearable system of claim 1 comprising a boot.

6. A method comprising:
for each of a plurality of nerve stimulation electrode arrangements, delivering energy to tissue;
for each of a plurality of nerve recording electrode arrangements, sensing nerve responses to delivered energy;
based at least in part on the responses, selecting an optimal one of the nerve stimulation electrode arrangements and selecting an optimal one of the nerve recording electrode arrangements; and operating a wearable neurostimulation device using the optimal one of the nerve stimulation electrode arrangements and using the optimal one of the nerve recording electrode arrangements, wherein the operating comprises acquiring nerve conduction information.

7. The method of claim 6 comprising
receiving nerve information via the optimal one of the nerve recording electrode arrangements responsive to delivery of nerve stimulation via the optimal one of the nerve stimulation recording electrodes, wherein the nerve information comprises the nerve conduction information;
analyzing at least a portion of the nerve information; and
based at least in part on the analyzing, determining at least one value of at least one operational parameter of the wearable neurostimulation device.

8. The method of claim 7 wherein the analyzing comprises analyzing the at least a portion of the nerve information for peripheral neuropathy.

9. The method of claim 7 wherein the analyzing comprises analyzing the at least a portion of the nerve information for nerve conduction of at least two nerves.

10. The method of claim 7 wherein the analyzing comprises analyzing velocity of nerve conduction, latency of nerve conduction and amplitude of nerve conduction.

11. The method of claim 7 wherein the analyzing comprises analyzing duration of at least one nerve conduction waveform.

12. The method of claim 7 wherein the analyzing comprises analyzing changes with respect to time of one or more of latency, conduction velocity, amplitude and duration.

13. The method of claim 7 wherein the analyzing comprises determining whether one or more parameter values are in an acceptable range or in range indicative of neuropathy.

14. The method of claim 6 wherein the optimal one of the nerve stimulation electrode arrangements is above an ankle and the optimal one of the nerve recording electrode arrangements is below the ankle.

15. The non-invasive wearable system of claim 1 wherein the circuitry that selects an optimal one of the plurality of different acquisition arrays selects the optimal one of the plurality of different acquisition arrays as being, with respect to a lower leg, distal to the selected optimal one of the plurality of different stimulation arrays.

16. The non-invasive wearable system of claim 1 wherein the circuitry that selects an optimal one of the plurality of different acquisition arrays selects the optimal one of the plurality of different acquisition arrays as being, with respect to a lower leg, closer to toes than the selected optimal one of the plurality of different stimulation arrays.

17. The non-invasive wearable system of claim 1 wherein the circuitry that selects the optimal one of the plurality of different stimulation arrays and selects the optimal one of the plurality of different acquisition arrays selects the optimal one of the plurality of different acquisition arrays as being, with respect to a lower leg, below an ankle and selects the optimal one of the plurality of different stimulation arrays as being, with respect to the lower leg, above the ankle.

18. One or more non-transitory computer-readable media comprising processor-executable instructions executable to instruct a wearable neurostimulation device to:
for each of a plurality of nerve stimulation electrode arrangements, deliver energy to tissue;
for each of a plurality of nerve recording electrode arrangements, sense nerve responses to delivered energy;
based at least in part on the responses, select an optimal one of the nerve stimulation electrode arrangements and select an optimal one of the nerve recording electrode arrangements;
operate the wearable neurostimulation device using the optimal one of the nerve stimulation electrode arrangements and using the optimal one of the nerve recording electrode arrangements; and
during operation of the wearable neurostimulation device, acquire nerve conduction information.

* * * * *